United States Patent
Tanaka et al.

(10) Patent No.: US 6,436,922 B1
(45) Date of Patent: *Aug. 20, 2002

(54) 5,11-DIHYDROBENZO[B,E][1,4]OXAZEPINE DERIVATIVES AND PHARMACEUTICAL COMPOSITIONS CONTAINING THE SAME

(75) Inventors: Yuji Tanaka; Keiji Misumi; Yoshinari Kawakami; Masahiko Moriguchi; Kazuyoshi Takahashi; Hiroki Okamoto; Toshiaki Kamisaki; Kimihiro Inoue; Makoto Sato, all of Shiga-Ken (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/597,409

(22) Filed: Jun. 19, 2000

Related U.S. Application Data

(63) Continuation of application No. 09/147,012, filed as application No. PCT/JP97/00754 on Mar. 11, 1997, now Pat. No. 6,127,361.

(30) Foreign Application Priority Data

Mar. 11, 1996 (JP) ................................................ 8-83104

(51) Int. Cl.$^7$ ..................... A61K 31/553; C07D 267/18; A61P 1/00
(52) U.S. Cl. ................... 514/211.11; 540/550
(58) Field of Search ...................... 540/550; 514/211.11

(56) References Cited

FOREIGN PATENT DOCUMENTS

| EP | 0 404 359 | 12/1990 |
| WO | 93/09104 | 5/1993 |

*Primary Examiner*—Brenda Coleman
(74) *Attorney, Agent, or Firm*—Oblon, Spivak, McClelland, Maier & Neustadt, P.C.

(57) ABSTRACT

Disclosed are 5,11-Dihydrodibenzo[b,e][1,4]oxazepine derivatives such as (R)-(+)-5,11-dihydro-5-[1-(4-methoxyphenethyl)-2-pyrrolidinylmethyl]dibenzo[b,e][1,4]oxazepine and (R)-(+)-5,11-dihydro-5-[1-(4-fluorophenethyl)-2-pyrrolidinylmethyl]dibenzo[b,e][1,4]oxazepine, stereoisomers thereof, pharmacologically acceptable salts thereof, or hydrates thereof and a pharmaceutical composition conating the 5,11-Dihydrodibenzo[b,e][1,4]oxazepine derivatives. The derivatives have an excellent activity of improving a digestive tract moving function and are free of side effect.

8 Claims, No Drawings

5,11-DIHYDROBENZO[B,E][1,4]OXAZEPINE DERIVATIVES AND PHARMACEUTICAL COMPOSITIONS CONTAINING THE SAME

This application is a continuation of U.S. application Ser. No. 09/147,012, filed Sep. 11, 1998, now U.S. Pat. No. 6,127,361 which is a national stage entry under 35 U.S.C. §371 of PCT/JP97/00754, filed on Mar. 11, 1997.

FIELD OF THE INVENTION

The present invention relates to 5,11-dihydrodibenzo[b,e][1,4]oxazepine derivatives, stereoisomers thereof, pharmacologically acceptable salts thereof or hydrates thereof, which have a calcium channel blocking activity and are useful for the therapy and the treatment of the digestive tract abnormal moving function diseases, especially the intestinal diseases such as the irritable bowel syndrome as well as a pharmaceutical composition containing the same as an active ingredient.

BACKGROUND OF THE INVENTION

For example, European Patent No. 0404359A1 discloses that 5,11-dihydrodibenzo[b,e][1,4]thiazepine derivatives are useful as a calcium channel blocker having a selectivity for the gastrointestinal tract. Quinn, P. et al., Brit. J. Pharmacol. 1994, 112(Suppl.), Abst p573 and Wallis, R. M. et al., Brit. J. Pharmacol. 1994, 112(Suppl.), Abst p574 disclose that (S)-5-[1-[2-(Methoxyphenyl)ethyl]pyrrolidin-2-ylmethyl]-5,11-dihydrodibenzo[b,e][1,4]thiazepine maleate which is one of the above-mentioned derivatives has the same activity as mentioned above. However, the above-mentioned compounds are problematic in that they exhibit an anticholinergic activity which gives a side effect such as hydrodipsia, mydriasis or the like.

In recent years, as the social environment has become complicated, a lot of people have come to be under great stress, and there have been a large number of patients suffering from an irritable bowel syndrome of which main symptoms are abnormal bowel movement, abdominal pain and the like. To cope with such diseases, an anticholinergic agent, a laxative agent, an antidiarrheal drug, a drug for controlling intestinal function, a mucosa paralyzant, a drug for controlling an intestinal tract moving function, an agent of controlling an autonomic nerve, a herb medicine, an antianxiety agent, an antidepressant, a hypnotic agent, a neuroleptic agent and the like have been used so far. However, clinical effects of these agents are insufficient, and these agents are not necessarily satisfactory in view of the side effects. Accordingly, the development of a new type of a drug which is free of a side effect and which has an excellent activity of improving a digestive tract moving function has been in demand.

DISCLOSURE OF THE INVENTION

An object of the present invention is to provide a novel compound having an excellent activity of improving a digestive tract moving function.

Another object of the present invention is to provide a novel compound which is free of a side effect and which has an excellent activity of improving a digestive tract moving function.

Another object of the present invention is to provide a pharmaceutical composition containing said compound.

These and other objects of the present invention will be apparent from the following description and examples.

It has been considered that since a calcium channel blocker exhibits an activity of inhibiting contraction of a smooth muscle, it is effective for treating diseases caused by abnormal acceleration of contraction of the intestinal tract, for example, intestinal diseases such as an irritable bowel syndrome. In fact, it has been reported that a calcium channel blocker such as nicardipine, verapamil or the like is effective for treating an irritable bowel syndrome [Am. J. Gastroenterol., 80, 317 (1985), Gut., 28, 1609 (1987), J. Clin, Psychiatry., 48, 388 (1987), and Pharmacol. Ther., 60, 121 (1993)]. Actually, however, this calcium channel blocker is little applied clinically owing to its main effect on the heart blood vessel system. Under these circumstances, the present inventors have assiduously conducted investigations to develop a calcium channel blocker which exhibits a low toxicity, namely which gives no influence to the heart blood vessel system and which has a selectivity for the intestinal tract as an agent of treating the digestive tract abnormal moving function diseases, especially the intestinal diseases such as the irritable bowel syndrome. As a result, they have found that a compound represented by formula [I] gives a calcium channel antagonism selectively to the intestinal tract, and that it is effective as an agent of improving a digestive tract abnormal moving function which is almost free from side effects such as an anticholinergic activity, a decrease in the body temperature and the like. These findings have led to the completion of the present invention. That is, the present invention relates to 5,11-dihydrodibenzo[b,e][1,4]oxazepine derivatives represented by formula [I]:

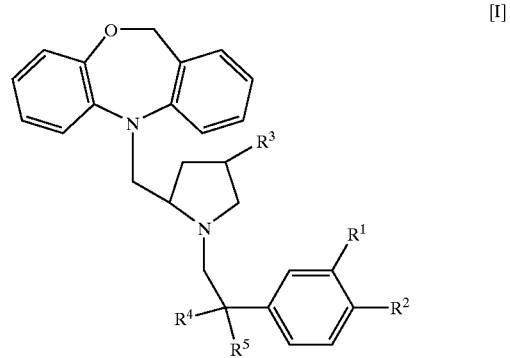

[I]

wherein $R^1$ and $R^2$ are the same or different and each represents a hydrogen atom, a halogen atom, a cyano group, a hydroxy group or a lower alkoxy group, or $R^1$ and $R^2$ together form —O(CH$_2$)nO— in which n is 1, 2 or 3, $R^3$ represents a hydrogen atom or hydroxy group, $R^4$ and $R^5$ are the same or different and each represents a hydrogen atom or hydroxy group, or $R^4$ and $R^5$ together form =O group, stereoisomers thereof, pharmacologically acceptable salts thereof, or hydrates thereof as well as a pharmaceutical composition containing the same as an active ingredient.

DESCRIPTION OF THE PREFERRED EMBODIMENTS

In formula [I], examples of the halogen atom of $R^1$ and $R^2$ include fluorine and chlorine atoms. Examples of the lower alkoxy group include an alkoxy group having 1 to 5 carbon atoms such as methoxy, ethoxy and n-propoxy groups. Examples of —O(CH$_2$)$_n$O— include methylenedioxy, ethylenedioxy and propylenedioxy groups. Among these, fluorine atom is preferable as the halogen atom, and an alkoxy group having 1 to 3 carbon atoms is preferable as the lower alkoxy group.

In the present invention, it is preferable that $R^3$, $R^4$ and $R^5$ in the formula [I] each be a hydrogen atom. In this connection, it is preferable that $R^1$ and $R^2$ in the formula [I] be the same or different and each represent a hydrogen atom, a halogen atom or a lower alkoxy group, provided that the both $R^1$ and $R^2$ do not represent a hydrogen atom at the same time. Furthermore, it is more preferable that $R^1$ represent a hydrogen atom, and $R^2$ represent a halogen atom or a lower alkoxy group. Among these, the most preferred are (R)-(+)-5,11-dihydro-5-[1-(4-methoxyphenethyl)-2-pyrrolidinylmethyl]dibenzo[b,e][1,4]oxazepine having the following formula, pharmacologically acceptable salts thereof and hydrates thereof.

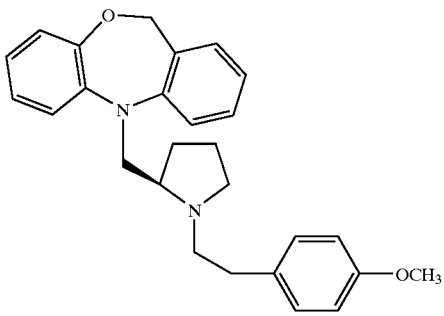

(R)-(+)-5,11-dihydro-5-[1-(4-fluorophenethyl)-2-pyrrolidinylmethyl]dibenzo[b,e][1,4]oxazepine, pharmacologically acceptable salts thereof and hydrates thereof are also the most preferable.

Examples of the pharmacologically acceptable salts of Compounds [I] in the present invention include mineral (inorganic) acid salts such as a hydrochloride, a hydrobromide, a sulfate and a phosphate; and organic acid salts such as an acetate, a lactate, a fumarate, a maleate, a malate, a tartrate, a citrate, an oxalate, an aspartate and a methanesulfonate. Among these, inorganic acid salt is preferred.

Compounds [I] of the present invention have one asymmetric carbon atom, and can include optical isomers. These optical isomers, mixtures thereof or racemic compounds thereof are included in Compounds [I] of the present invention. In this connection, the R form is preferred. Further, Compounds [I] and the pharmacologically acceptable salts thereof in the present invention may be present in the form of hydrates or solvates. Thus, these hydrates or solvates are also included in the present invention.

Compound [I] of the present invention can be produced as schematically shown below, for example.

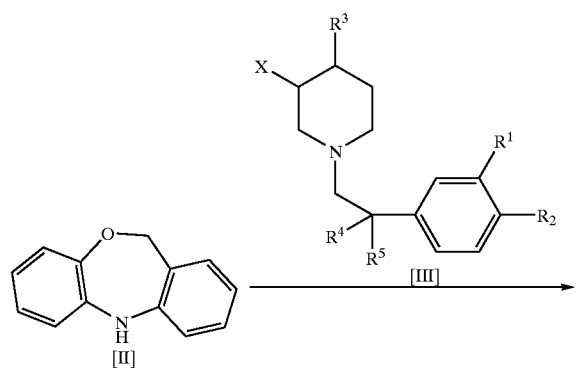

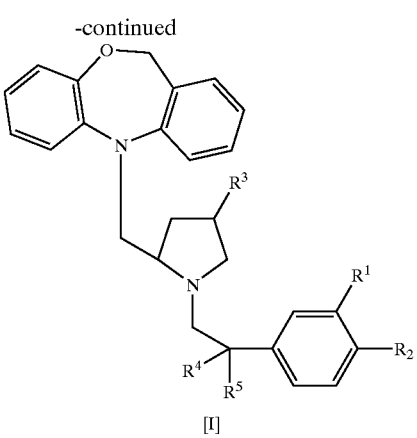

wherein $R^1$ to $R^5$ are as defined above, and X represents a chlorine atom, a bromine atom or an iodine atom. In this respect, it is preferable that $R^3$, $R^4$ and $R^5$ each represents a hydrogen atom.

Compound [I] of the present invention can be produced by reacting Compound [II] with a halogen compound represented by formula [III] in a solvent in the presence of a base.

Preferable examples of the reaction solvent include dimethyl sulfoxide; amides such as N,N-dimethylformamide; ethers such as tetrahydrofuran, diethyl ether, dioxane and 1,2-dimethoxyethane; toluene; xylene and benzene. Examples of the base include sodium hydride, potassium hydride, lithium diisopropylamide, n-butyl lithium, sodium methoxide and potassium tert-butoxide.

The reaction temperature is usually between 0° C. and 150° C., preferably between room temperature and 100° C.

The reaction time varies depending on the reaction temperature or the type of the solvent. It is usually between 1 and 150 hours.

The amount of Compound [III] or the amount of the base is 1 mol or more, preferably between 1 and 5 mols per mol of Compound [II].

Compound [II] used as a starting material in the above-mentioned reaction can be formed by a known method [J. Med. Chem., 7, 609 (1964)].

The halogen compound of formula [III] can be produced according to a known method [EP 0404359A1].

The stereochemistry of the compounds in the present invention was determined on the basis of the reaction mechanism described in the literature [EP 0404359A1 and Tetrahedron, 37, 2173 (1981)].

When the compound of the present invention is used in the form of pharmaceutical preparations or compositions, it is possible that the above-mentioned compound is mixed with preparation auxiliaries such as an excipient, a carrier, a diluent and the like as required, the mixture is formed into tablets, capsules, granules, grains, powders, pills, syrups, suspensions, emulsifiers, ointments, suppositories, injections or the like, and the resulting preparations are administered either orally or parenterally. In this connection, it is preferable that the pharmaceutical preparations or compositions contain the compound of the present invention as an active ingredient, and pharmaceutically acceptable carrier and/or diluent. Examples of the carrier and diluent include glucose, sucrose, lactose, talc, silica, cellulose, methyl cellulose, starch, gelatin, ethylene glycol, polyethylene glycol, glycerin, ethanol, water, fat and oil.

The dose and the number of administrations of the compound in the present invention can be selected, as required, depending on the type of the disease and the age, the weight and the like of the patient. For example, when the compound of the present invention is orally administered to a grown-up patient suffering from an intestinal disease such as an irritable bowel syndrome, it may be administered at a dose of from approximately 0.1 to 1,000 mg a day either once or in divided portions.

EXAMPLES

The present invention is illustrated specifically by referring to the following Examples, Test Examples and Preparation Examples. However, the present invention is not limited thereto unless deviating from the scope thereof.

Example 1

Sixty-percent sodium hydride (520 mg, 13 mmols) was washed with petroleum ether, and then suspended in 55 ml of dimethyl sulfoxide. To the suspension were added 2.0 g (10 mmols) of 5,11-dihydrodibenzo[b,e][1,4]oxazepine. The mixture was stirred in a nitrogen atmosphere at room temperature for 40 minutes. To this reaction solution was added dropwise a solution of 3.1 g (12 mmols) of (S)-(+)-3-chloro-1-(4-methoxyphenethyl)piperidine[[$\alpha$]$D^{25}$=+10.1° (c=1.2, ethanol)] in 10 ml of dimethyl sulfoxide, and the mixed solution was stirred at room temperature for 14 hours and at 40° C. for 6 hours. The reaction solution was poured into ice water, and extracted with ethyl acetate. The organic layer was washed with water and with a saturated aqueous solution of sodium chloride in this order, and dried. Subsequently, the solvent was distilled off under reduced pressure. The resulting residue was subjected to column chromatography, and eluted with a mixed solvent of ethyl acetate and hexane at a ratio of 1:2. This mixed solvent was distilled off under reduced pressure to give 2.9 g of (R)-(+)-5,11-dihydro-5-[1-(4-methoxyphenethyl)-2-pyrrolidinylmethyl]dibenzo[b,e][1,4]oxazepine as a pale yellow oil in a yield of 70%.

[$\alpha$]$D^{25}$+35.4° (c=1.1, EtOH)

IR (film) ν max cm$^{-1}$: 1610, 1515, 1490, 1465, 1350, 1300

FAB/Mass: 415 [M+H]$^+$

NMR (CDCl$_3$) δ: 1.57–1.87(4H,m), 2.20–2.30(1H,m), 2.47–2.58(1H,m), 2.73–2.79(3H,m), 2.99–3.10(1H,m), 3.19–3.22(1H,m), 3.35(1H, dd, J=9.4, 13.0 Hz), 3.81(3H,s), 4.10(1H, dd, J=3.6, 13.0 Hz), 5.21(1H, d, J=11.7 Hz), 5.33(1H, d, J=11.7 Hz), 6.72–6.85(3H,m), 6.86(2H, d, J=8.7 Hz), 6.92–7.20 (3H,m), 7.14 (2H, d, J=8.7 Hz), 7.20–7.35 (2H,m)

Elemental analysis: for $C_{27}H_{30}N_2O_2$

Calculated (%): C, 78.23; H, 7.29; N, 6.76.

Found (%): C, 78.13; H, 7.59; N, 6.57.

Example 2

A hydrogen chloride ether saturated solution was added to a solution of 2.9 g (7.0 mmols) of (R)-(+)-5,11-dihydro-5-[1-(4-methoxyphenethyl)-2-pyrrolidinylmethyl]dibenzo[b,e][1,4]oxazepine in 20 ml of dichloromethane, and the mixture was stirred for 5 minutes. Then, the solvent was distilled off under reduced pressure. The resulting residue was recrystallized from a mixed solvent of dichloromethane and diethyl ether to give 2.9 g of (R)-(+)-5,11-dihydro-5-[1-(4-methoxyphenethyl)-2-pyrrolidinylmethyl]-dibenzo[b,e][1,4]oxazepine hydrochloride as a colorless prism crystal in a yield of 93%.

m.p.: 173–175 C

[$\alpha$]$D^{25}$+2.5° (c=1.0, EtOH)

IR (nujol) ν max cm$^{-1}$: 2390, 1510, 1490, 1465, 1255

FAB/Mass: 415 [M+H]$^+$

NMR (CDCl$_3$) δ: 1.85–2.40(4H,m), 2.68–3.68(6H,m), 3.80(3H,s), 3.84–4.02(1H,m), 4.26(1H, dd, J=13.9, 8.3 Hz), 4.68(1H, dd, J=13.9, 4.8 Hz), 5.17(1H, d, J=12.3 Hz), 5.30(1H, d. J=12.3 Hz), 6.76–6.96(5H,m), 6.97–7.20(5H,m), 7.20–7.40(2H,m), 12.65–12.95(1H,br) Elemental analysis: for $C_{27}H_{30}N_2O_2.HCl.0.1H_2O$ Calculated (%): C, 71.62; H, 6.95; N, 6.19.

Found (%): C, 71.45; H, 6.95; N, 6.39.

Example 3

Four-hundred milligrams (9.9 mmols) of 60% sodium hydride were washed with petroleum ether, and then suspended in 40 ml of dimethyl sulfoxide. To the suspension were added 1.5 g (7.6 mmols) of 5,11-dihydrodibenzo[b,e][1,4]oxazepine. The mixture was stirred in a nitrogen atmosphere at room temperature for 1 hour. To this reaction solution was added dropwise a solution of 2.2 g (9.1 mmols) of (S)-(+) -3-chloro-1-(4-fluorophenethyl)piperidine[[$\alpha$]$D^{25}$=+9.5° (c=1.0, ethano 1)] in 10 ml of dimethyl sulfoxide, and the mixed solution was stirred at room temperature for 4 days. The reaction solution was poured into ice water, and extracted with ethyl acetate. The organic layer was washed with water and with a saturated aqueous solution of sodium chloride in this order, and dried. Subsequently, the solvent was distilled off under reduced pressure. The resulting residue was subjected to column chromatography, and eluted with a mixed solvent of ethyl acetate and hexane at a ratio of 1:2. This mixed solvent was distilled off under reduced pressure to give 1.4 g of (R)-(+)-5,11-dihydro-5-[1-(4-fluorophenethyl)-2-pyrrolidinyl methyl]dibenzo[b,e][1,4]oxazepine as a pale yellow oil in a yield of 44%.

[$\alpha$]$D^{25}$+39.5° (c=1.0, EtOH)

IR (film) ν max cm$^{-1}$: 1600, 1510, 1490, 1460, 1300, 1265, 1220

FAB/Mass: 403 [M+H]$^+$

NMR (CDCl$_3$ ) δ: 1.55–1.94(4H,m), 2.15–2.31(1H,m), 2.45–2.63(1H,m), 2.67–2.90(3H,m), 2.95–3.12(1H,m), 3.12–3.26(1H,m), 3.36(1H, dd, J=9.3, 13.0 Hz), 4.06(1H, dd, J=3.6, 13.0 Hz), 5.21(1H, d, J=11.8 Hz), 5.32(1H, d, J=11.8 Hz), 6.70–6.88(3H,m), 6.90–7.20(7H,m), 7.20–7.37 (2H,m)

Elemental analysis: for $C_{26}H_{27}FN_2O$

Calculated (%): C, 77.58; H, 6.76; N, 6.96.

Found (%): C, 77.28; H, 7.02; N, 6.89.

Example 4

A hydrogen chloride ether saturated solution was added to a solution of 1.2 g (3.1 mmols) of (R)-(+)-5,11-dihydro-5-[1-(4-fluorophenethyl)-2-pyrrolidinylmethyl]dibenzo[b,e][1,4]oxazepine in 10 ml of dichloromethane, and the mixture was stirred for 5 minutes. Then, the solvent was distilled off under reduced pressure. The resulting residue was recrystallized from a mixed solvent of acetone and diethyl ether to give 1.2. g of (R)-(+)-5,11-dihydro-5-[1-(4-fluorophenethyl)-2-pyrrolidinylmethyl]dibenzo[b,e][1,4]oxazepine hydrochloride as a pale yellow prism crystal in a yield of 87%.

m.p.: 172–175° C.

[$\alpha$]$D^{25}$+6.0° (c=1.0, EtOH)

IR (nujol)ν max cm$^{-1}$: 2390, 1510, 1490, 1465, 1220

FAB/Mass: 403 [M+H]$^+$

NMR (CDCl$_3$): 1.85–2.37(4H,m), 2.68–3.70(6H,m), 3.82–4.04(1H,m), 4.26(1H, dd, J=14.0, 7.9 Hz), 4.69(1H, dd, J=14.0, 5.2 Hz), 15 5.15(1H, d, J=12.4 Hz), 5.30(1H, d, J=12.4 Hz), 6.75–6.90(3H,m), 6.90–7.40(9H,m), 12.75–13.05(1H,br)

Elemental analysis: for $C_{26}H_{27}FN_2O\cdot HCl$

Calculated (%): C, 71.14; H, 6.43; N, 6.38.

Found (%): C, 71.08; H, 6.53; N, 6.35.

Example 5

Sixty-percent sodium hydride (608 mg, 15 mmols) was washed with petroleum ether, and then suspended in 50 ml of dimethyl sulfoxide. To the suspension were added 1.5 g (7.6 mmols) of 5,11-dihydrodibenzo[b,e][1,4]oxazepine. The mixture was stirred in a nitrogen atmosphere at room temperature for 1 hour. To this reaction solution was added dropwise a solution of 3.2 g (14 mmols) of (S)-(+) -3-chloro-1-phenethylpiperidine[[α]$D^{25}$=+10.9° (c=1.0, ethanol)] in 30 ml of dimethyl sulfoxide, and the mixed solution was stirred at room temperature for 2.5 hours and at 45° C. for 6 hours. The reaction solution was poured into ice water, and extracted with ethyl acetate. The organic layer was washed with water and with a saturated aqueous solution of sodium chloride in this order, and dried. Subsequently, the solvent was distilled off under reduced pressure. The resulting residue was subjected to column chromatography, and eluted with a mixed solvent of ethyl acetate and hexane at a ratio of 1:2. This mixed solvent was distilled off under reduced pressure to give 3.5 g of (R)-(+)-5,11-dihydro-5-[1-phenethyl-2-pyrrolidinyl-methyl]dibenzo[b,e][1,4]oxazepine as a pale yellow oil in a yield of 91%.

[α]$D^{25}$+42.3° (c=1.0, EtOH)

IR (film) ν max $cm^{-1}$: 1605, 1490, 1460, 1350, 1300

FAB/Mass: 385 $[M+H]^+$

NMR ($CDCl_3$) δ: 1.55–1.90(4H,m), 2.17–2.33(1H,m), 2.50–2.67(1H,m), 2.70–2.92(3H,m), 3.00–3.27(2H,m), 3.30–3.45(1H,m), 4.03–4.15(1H,m), 5.20(1H, d, J=11.7 Hz), 5.32(1H, d, J=11.7 Hz), 6.70–7.40(13H,m),

Elemental analysis: for $C_{26}H_{28}N_2O$

Calculated (%): C, 81.21; H, 7.34; N, 7.29.

Found (%): C, 81.55; H, 7.06; N, 7.23.

Example 6

A hydrogen chloride ether saturated solution was added to a solution of 1.9 g (4.9 mmols) of (R)-(+)-5,11-dihydro-5-[1-phenethyl-2-pyrrolidinylmethyl]dibenzo[b,e][1,4] oxazepine in 50 ml of diethyl ether, and the mixture was stirred for 5 minutes. Then, the solvent was distilled off under reduced pressure. The resulting residue was recrystallized from acetone to give 1.7 g of (R)-(+)-5,11-dihydro-5-[1-phenethyl-2-pyrrolidinylmethyl]dibenzo[b,e][1,4] oxazepine hydrochloride as a colorless prism crystal in a yield of 84%.

m.p.: 179–182° C.

[α]$D^{25}$+7.80 (c=1.0, EtOH)

IR (nujol)ν max $cm^{-1}$: 2400, 1490, 1465, 1260

FAB/Mass: 385 $[M+H]^+$

NMR ($CDCl_3$) δ: 1.80–2.35(4H,m), 2.72–3.22(3H,m), 3.30–3.70(3H,m), 3.82–4.02(1H,m), 4.20–4.38(1H,m), 4.60–4.77(1H,m), 5.15(1H, d, J=12.3 Hz), 5.30(1H, d. J=12.3 Hz), 6.75–7.40 (13H,m), 12.80 (1H,br)

Elemental analysis: for $C_{26}H_{28}N_2O\cdot HCl$

Calculated (%): C, 74.18; H, 6.94; N, 6.65.

Found (%): C, 74.27; H, 6.99; N, 6.54.

Example 7

Sixty-percent sodium hydride (470 mg, 12 mmols) was washed with petroleum ether, and then suspended in 50 ml of dimethyl sulfoxide. To the suspension were added 1.5 g (7.5 mmols) of 5,11-dihydrodibenzo[b,e][1,4]oxazepine. The mixture was stirred in a nitrogen atmosphere at room temperature for 30 minutes. To this reaction solution was added dropwise a solution of 3.2 g (11 mmols) of (S)-(+)-3-chloro-1-(3,4-dimethoxyphenethyl)piperidine[[α]$D^{25}$=+20.3 ° (c=0.9, ethano 1)] in 30 ml of dimethyl sulfoxide, and the mixed solution was stirred at 50° C. for 5 hours. The reaction solution was poured into ice water, and extracted with ethyl acetate. The organic layer was washed with water and with a saturated aqueous solution of sodium chloride in this order, and dried. Subsequently, the solvent was distilled off under reduced pressure. The resulting residue was subjected to column chromatography, and eluted with a mixed solvent of ethyl acetate and hexane at a ratio of 1:3. This mixed solvent was distilled off under reduced pressure. Further, the thus-obtained residue was subjected to column chromatography, and eluted with a mixed solvent of chloroform and methanol at a ratio of 300:1. The mixed solvent was then distilled off under reduced pressure to give 2.8 g of (R)-(+)-5,11-dihydro-5-[1-(3,4-dimethoxyphenethyl)-2-pyrrolidinylmethyl]dibenzo[b,e][1,4]oxazepine as a pale yellow oil in a yield of 85%.

[α]$D^{25}$+30.6° (c=1.0, EtOH)

IR (film) ν max $cm^{-1}$: 1576, 1516, 1492, 1464, 1264, 1236

FAB/Mass: 445 $[M+H]^+$

NMR ($CDCl_3$) δ: 1.60–1.94(4H,m), 2.16–2.32(1H,m), 2.46–2.64(1H,m), 2.66–2.86(3H,m), 2.95–3.25(2H,m), 3.39 (1H, dd, J=9.3, 13.0 Hz), 3.88(3H,s), 3.89(3H,s), 4.10(1H, dd, J=3.5, 13.0 Hz), 5.21(1H, d, J=11.8 Hz), 5.33(1H, d, J=11.8 Hz), 6.66–7.40(11H,m)

Elemental analysis: for $C_{28}H_{32}N_2O_3$

Calculated (%): C, 75.33; H, 7.27; N, 6.28.

Found (%): C, 75.03; H, 7.03; N, 6.11.

Example 8

A hydrogen chloride ether saturated solution was added to a solution of 1.5 g (3.4 mmols) of (R)-(+)-5,11-dihydro-5-[1-(3,4-dimethoxyphenethyl)-2-pyrrolidinylmethyl]dibenzo [b,e][1,4]oxazepine in 30 ml of diethyl ether, and the mixture was stirred for 5 minutes. Then, the solvent was distilled off under reduced pressure. The resulting residue was recrystallized from acetone to give 1.4 g of (R) -(+)-5,11-dihydro-5-[1-(3,4-dimethoxyphenethyl)-2-pyrrolidinyl-methyl] dibenzo[b,e][1,4]oxazepine hydrochloride as a colorless prism crystal in a yield of 88%.

m.p.: 106–109° C.

[α]$D^{25}$+0.30 (c=1.0, EtOH)

IR (nujol) ν max $cm^{-1}$: 2855, 1515, 1490, 1465, 1265

FAB/Mass: 445 $[M+H]^+$

NMR ($CDCl_3$) δ: 1.60–2.50(4H,m), 2.60–4.15(13H,m), 4.26(1H,m), 4.68(1H,m), 5.16(1H, d, J=12.5 Hz), 5.32(1H, d, J=12.5 Hz), 6.70–7.40 (11H,m), 12.67 (1H,br)

Elemental analysis: for $C_{28}H_{32}N_2O_3\cdot HCl\cdot 1.2H_2O$

Calculated (%): C, 66.89; H, 7.10; N, 5.57.

Found (%): C, 66.77; H, 6.86; N, 5.85.

Example 9

Three-hundred milligrams (7.5 mmols) of 60% sodium hydride were washed with petroleum ether, and then suspended in 30 ml of dimethyl sulfoxide. To the suspension were added 1.4 g (7.1 mmols) of 5,11-dihydrodibenzo[b,e] [1,4]oxazepine. The mixture was stirred in a nitrogen atmosphere at room temperature for 40 minutes. To this reaction solution was added dropwise a solution of 1.7 g (6.8 mmols) of (S)-(+)-3-chloro-1-(4-cyanophenethyl)piperidine [[α] $D^{25}$=+16.7° (c=0.5, ethanol)] in 10 ml of dimethyl sulfoxide, and the mixed solution was stirred at room temperature for 17 hours and at 40° C. for 6 hours. The reaction solution was poured into ice water, and extracted with ethyl acetate. The organic layer was washed with water and with a saturated aqueous solution of sodium chloride in this order, and dried. Subsequently, the solvent was distilled off under reduced pressure. The resulting residue was subjected to column chromatography, and eluted with a mixed solvent of ethyl acetate and hexane at a ratio of 1:2. This mixed solvent was distilled off under reduced pressure to give 0.4 g of (R)-(+)-5,11-dihydro-5-[1-(4-cyanophenethyl)-2-pyrrolidinylmethyl]dibenzo[b,e][1,4]oxazepine as a pale yellow oil in a yield of 14%.

$[\alpha]D^{25}$+43.6° (c=0.1, EtOH)

IR (film) ν max cm$^{-1}$: 2230, 1610, 1575, 1490, 1195

FAB/Mass: 410 [M+H]$^+$

NMR (CDCl$_3$) δ: 1.55–1.90(4H,m), 2.20–2.30(1H,m), 2.50–2.65(1H,m), 2.70–2.90(3H,m), 3.00–3.12(1H,m), 3.13–3.23(1H,m), 3.37(1H, dd, J=8.9, 13.1 Hz), 3.97(1H, dd, J=3.9, 13.1 Hz), 5.20(1H, d, J=11.8 Hz), 5.31(1H, d, J=11.8 Hz), 6.75–6.88(3H,m), 6.90–7.02(1H,m), 7.02–7.10(2H,m), 7.23–7.35(2H,m), 7.30(2H, d, J=8.2 Hz), 7.59(2H, d, J=8.2 Hz)

Elemental analysis: for C$_{27}$H$_{27}$N$_3$O

Calculated (%): C, 79.19; H, 6.65; N, 10.26.

Found (%): C, 79.09; H, 6.72; N, 10.15.

Example 10

A hydrogen chloride ether saturated solution was added to a solution of 0.4 g (1.0 mmol) of (R)-(+)-5,11-dihydro-5-[1-(4-cyanophenethyl)-2-pyrrolidinylmethyl]dibenzo[b,e][1,4]oxazepine in 2 ml of dichloromethane, and the mixture was stirred for 5 minutes. Then, the solvent was distilled off under reduced pressure. The resulting residue was recrystallized from a mixed solvent of dichloromethane and diethyl ether to give 0.35 g (78%) of (R)-(+)-5,11-dihydro-5-[1-(4-cyanophenethyl)-2-pyrrolidinyl methyl]dibenzo[b,e][1,4]oxazepine hydrochloride as a colorless prism crystal in a yield of 78%.

m.p.: 109–112° C.

$[\alpha]D^{25}$+10.8° (c=0.2, CHCl$_3$)

IR (nujol) ν max cm$^{-1}$: 2230, 1490, 1260

FAB/Mass: 410 [M+H]$^+$

NMR (CDCl$_3$) δ: 1.85–2.10(1H,m), 2.15–2.40(3H,m), 2.70–2.90(1H,m), 2.90–3.10(1H,m), 3.10–3.30(1H,m), 3.42–3.60(2H,m), 3.60–3.80 (1H,m), 3.87–4.03(1H,m), 4.27(1H, dd, J=14.1, 7.2 Hz), 4.71(1H, dd, J=14.1, 5.6 Hz), 5.13(1H, d, J=12.6 Hz), 5.31(1H, d, J=12.6 Hz), 6.88–7.00(3H,m), 7.00–7.40(5H,m), 7.34(2H, d, J=8.2 Hz), 7.63(2H, d, J=8.2 Hz), 12.90–13.10(1H, br)

Elemental analysis: for C$_{27}$H$_{27}$N$_3$O.HCl.0.5H$_2$O

Calculated (%): C, 71.27; H, 6.42; N, 9.24.

Found (%): C, 71.25; H, 6.20; N, 9.32.

Example 11

Sixty-percent sodium hydride (480 mg, 12 mmols) was washed with petroleum ether, and then suspended in 40 ml of dimethyl sulfoxide. To the suspension were added 2.0 g (10 mmols) of 5,11-dihydrodibenzo [b,e][1,4]oxazepine. The mixture was stirred in a nitrogen atmosphere at room temperature for 30 minutes. To this reaction solution was added dropwise a solution of 8.8 g (35 mmols) of (R)-(–)-3-chloro-1-(4-methoxyphenethyl)piperidine[[α]D$^{25}$=–7.4 (c=1.1, ethanol)] in 30 ml of dimethyl sulfoxide at room temperature, and the mixed solution was stirred for 90 hours. The reaction solution was poured into ice water, and extracted with ethyl acetate. The organic layer was washed with water and with a saturated aqueous solution of sodium chloride in this order, and dried. Subsequently, the solvent was distilled off under reduced pressure. The resulting residue was subjected to column chromatography, and eluted with a mixed solvent of ethyl acetate and hexane at a ratio of 1:2. This mixed solvent was distilled off under reduced pressure to give 12.0 g of (S)-(–)-5,11-dihydro-5-[1-(4-methoxyphenethyl)-2-pyrrolidinylmethyl]dibenzo[b,e][1,4]oxazepine as a pale yellow oil in a yield of 80%.

$[\alpha]D^{25}$–34.9° (c=1.0, EtOH)

IR (film) ν max cm$^{-1}$: The values agreed with those of the end compound in Example 1.

FAB/Mass : The value agreed with that of the end compound in Example 1.

NMR (CDCl$_3$) δ: The values agreed with those of the end compound in Example 1.

Example 12

A hydrogen chloride ether saturated solution was added to a solution of 12.0. g (23.2 mmols) of (S)-(–)-5,11-dihydro-5-(1-(4-methoxyphenethyl)-2-pyrrolidinylmethyl]dibenzo[b,e][1,4]oxazepine in 50 ml of dichloromethane, and the mixture was stirred for 5 minutes. Then, the solvent was distilled off under reduced pressure. The resulting residue was recrystallized from a mixed solvent of acetone and diethyl ether to give 9.5 g of (S)-(–)-5,11-dihydro-5-[1-(4-methoxyphenethyl)-2-pyrrolidinylmethyl]dibenzo[b,e][1,4]oxazepine hydrochloride as a colorless prism crystal in a yield of 73%.

m.p.: 175–179 ° C.

$[\alpha]D^{25}$–1.5° (c=1.0, EtOH)

IR (nujol) ν max cm$^{-1}$: The values agreed with those of the end compound in Example 2.

FAB/Mass : The value agreed with that of the end compound in Example 2.

NMR (CDCl$_3$) δ: The values agreed with those of the end compound in Example 2.

Elemental analysis: for C$_{27}$H$_{30}$N$_2$O$_2$.HCl

Calculated (%): C, 71.90; H, 6.93; N, 6.21.

Found (%): C, 71.91; H, 7.12; N, 6.11.

Example 13

Sixty-percent sodium hydride (0.34 g, 8.6 mmols) was washed with petroleum ether, and then suspended in 30 ml of dimethyl sulfoxide. To the suspension were added 1.38 g (7.0 mmols) of 5,11-dihydrodibenzo[b,e][1,4]oxazepine. The mixture was stirred in a nitrogen atmosphere at room temperature for 30 minutes. To this reaction solution was added dropwise a solution of 1.8 g (6.3 mmols) of (R)-(–)-3-chloro-1-(3,4-dimethoxyphenethyl)piperidine[[α]D$^{25}$=–20.3° (c=0.9, ethanol)] in 5 ml of dimethyl sulfoxide, and the mixed solution was stirred at room temperature for 12 hours and at 40° C. for 4 hours. The reaction solution was poured into ice water, and extracted with ethyl acetate. The organic layer was washed with water and with a saturated aqueous solution of sodium chloride in this order, and dried. Subsequently, the solvent was distilled off under reduced pressure. The resulting residue was subjected to column chromatography, and eluted with a mixed solvent of ethyl acetate and hexane at a ratio of 1:5. This mixed solvent was distilled off under reduced pressure. Further, the thus-obtained residue was subjected to column chromatography, and extracted with a mixed solvent of chloroform and methanol at a ratio of 200:1. This mixed solvent was then distilled off under reduced pressure to give 0.85 g of (S)-(−)-5,11-dihydro-5-[1-(3,4-dimethoxyphenethyl)-2-pyrrolidinyl-methyl]dibenzo[b,e][1,4]oxazepine as a pale yellow oil in a yield of 30%.

[α]D²⁵ −30.6° (c=1.0, EtOH)

IR (film) ν max cm⁻¹: The values agreed with those of the end compound in Example 9.

FAB/Mass: The value agreed with that of the end compound in Example 9.

NMR (CDCl₃) δ: The values agreed with those of the end compound in Example 9.

Elemental analysis: for C₂₈H₃₂N₂O₃

Calculated (%): C, 75.33; H, 7.27; N, 6.28.

Found (%): C, 75.03; H, 7.03; N, 6.11.

Example 14

A hydrogen chloride ether saturated solution was added to a solution of 0.85 g (1.9 mmols) of (S)-(−)-5,11-dihydro-5-[1-(3,4-dimethoxyphenethyl)-2-pyrrolidinylmethyl]dibenzo[b,e][1,4]oxazepine in 30 ml of diethyl ether, and the mixture was stirred for 5 minutes. Then, the solvent was distilled off under reduced pressure. The resulting residue was recrystallized from acetone to give 0.51 g of (S)-(−)-5,11-dihydro-5-[1-(3,4-dimethoxyphenethyl)-2-pyrrolidinylmethyl]dibenzo[b,e][1,4]oxazepine hydrochloride as a colorless prism crystal in a yield of 55%.

m.p.: 106–109° C.

[α]D²⁵ −0.3° (c=1.0, EtOH)

IR (nujol) ν max cm⁻¹: The values agreed with those of the end compound in Example 10.

FAB/Mass: The value agreed with that of the end compound in Example 10.

NMR (CDCl₃) δ: The values agreed with those of the end compound in Example 10.

Elemental analysis: for C₂₈H₃₂N₂O₃·HCl·1.2H₂O

Calculated (%): C, 66.89; H, 7.10; N, 5.57.

Found (%): C, 66.77; H, 6.86; N, 5.85.

Example 15

Sixty-percent sodium hydride (0.11 g, 2.8 mmols) was washed with petroleum ether, and then suspended in 10 ml of dimethyl sulfoxide. To the suspension were added 450 mg (2.3 mmols) of 5,11-dihydrodibenzo[b,e][1,4]oxazepine. The mixture was stirred in a nitrogen atmosphere at room temperature for 30 minutes. To this reaction solution was added dropwise a solution of 0.56 g (2.1 mmols) of (R)-(−)-3-chloro-1-(3,4-methylenedioxyphenethyl) piperidine [[α]D²⁵=−11.9° (c=1.0, ethanol)] in 5 ml of dimethyl sulfoxide, and the mixed solution was stirred at room temperature for 12 hours and at 40° C. for 4 hours. The reaction solution was poured into ice water, and extracted with ethyl acetate. The organic layer was washed with water and with a saturated aqueous solution of sodium chloride in this order, and dried. Subsequently, the solvent was distilled off under reduced pressure. The resulting residue was subjected to column chromatography, and eluted with a mixed solvent of ethyl acetate and hexane at a ratio of 1:5. This mixed solvent was distilled off under reduced pressure. Further, the thus-obtained residue was subjected to column chromatography, and eluted with a mixed solvent of chloroform and methanol at a ratio of 200:1. This mixed solvent was then distilled off under reduced pressure to give 0.46 g of (S)-(−)-5,11-dihydro-5-[1-(3,4-methylenedioxyphenethyl)-2-pyrrolidinyl-methyl]dibenzo[b,e][1,4]oxazepine as a pale yellow oil in a yield of 51%.

[α]D²⁵ −30.0° (c=1.0, EtOH)

IR (film) ν max cm⁻¹: 1600, 1576, 1492, 1464, 1446, 1298, 1250

FAB/Mass: 429 [M+H]+

NMR (CDCl₃) δ: 1.57–1.90(4H,m), 2.15–2.32(1H,m), 2.45–2.60(1H,m), 2.66–2.85(3H,m), 2.95–3.10(1H,m), 3.12–3.25(1H,m), 3.36(1H, dd, J=9.5, 12.9 Hz), 4.10(1H, dd, J=3.8, 12.9 Hz), 5.21(1H, d, J=11.8 Hz), 5.33(1H, d, J=11.8 Hz), 5.94(2H,s), 6.61–7.48(11H,m), Elemental analysis: for C₂₇H₂₈N₂O₃

Calculated (%): C, 75.66; H, 6.60; N, 6.54.

Found (%): C, 75.38; H, 6.67; N, 6.36.

Example 16

A hydrogen chloride ether saturated solution was added to a solution of 0.46 g (1.1 mmols) of (S)-(−)-5,11-dihydro-5-[1-(3,4-methylenedioxyphenethyl )-2-pyrrolidinylmethyl]dibenzo [b,e][1,4]oxazepine in 20 ml of diethyl ether, and the mixture was stirred for 5 minutes. Then, the solvent was distilled off under reduced pressure. The resulting residue was recrystallized from acetone to give 0.28 g of (S)-(+)-5,11-dihydro-5-[1-(3,4-methylenedioxyphenethyl)-2-pyrrolidinylmethyl]dibenzo [b,e][1,4]oxazepine hydrochloride as a colorless prism crystal in a yield of 56%.

m.p.: 158–162° C.

[α]D²⁵ +1.3° (c=1.0, EtOH)

IR (nujol) ν max cm⁻¹: 2395, 1490, 1465, 1255

FAB/Mass: 429 [M+H]⁺

NMR (CDCl₃) δ: 1.85–2.40(4H,m), 2.68–3.68(6H,m), 3.84–4.02(1H,m), 4.26(1H,m), 4.69(1H,m), 5.17(1H, d, J=12.5 Hz), 5.32(1H, d, J=12.5 Hz), 5.96(2H,s), 6.65–7.45 (11H,m), 12.80(1H,br)

Elemental analysis: for C₂₇H₂₈N₂O₃·HCl·0.2H₂O

Calculated (%): C, 69.20; H, 6.32; N, 5.98.

Found (%): C, 69.10; H, 6.28; N, 6.35.

Example 17

Sixty-percent sodium hydride (0.30 g, 7.5 mmols) was washed with petroleum ether, and then suspended in 30 ml of dimethyl sulfoxide. To the suspension were added 990 mg (5.0 mmols) of 5,11-5 dihydrodibenzo[b,e][1,4]oxazepine. The mixture was stirred in a nitrogen atmosphere at room temperature for 30 minutes. To this reaction solution was added dropwise a solution of 1.4 g (5.5 mmols) of (R)-(−)-3-chloro-1-(3-methoxyphenethyl)piperidine[[α]D²⁵=8.90° (c=1.2, ethanol)] in 5 ml of dimethyl sulfoxide, and the mixed solution was stirred at room temperature for 12 hours and at 45° C. for 2.5 hours. The reaction solution was poured into ice water, and extracted with ethyl acetate. The organic layer was washed with water and with a saturated aqueous solution of sodium chloride in this order, and dried. Subsequently, the solvent was distilled off under reduced pressure. The resulting residue was subjected to column chromatography, and eluted with a mixed solvent of ethyl acetate and hexane at a ratio of 1:5. This mixed solvent was then distilled off under reduced pressure. The thus-obtained residue was further subjected to column chromatography, and eluted with a mixed solvent of chloroform and methanol at a ratio of 200:1. This mixed solvent was distilled off under reduced pressure to give 1.64 g of (S)-(−)-5,11-dihydro-5-[1-(3-methoxyphenethyl)-2-pyrrolidinylmethyl]-dibenzo[b,e][1,4]oxazepine as a pale yellow oil in a yield of 79%.

$[\alpha]_D^{25}$ −32.4° (c=1.0, EtOH)

IR (film) ν max cm$^{-1}$: 1602, 1586, 1492, 1464, 1296, 1262

FAB/Mass: 415 [M+H]$^+$

NMR (CDCl$_3$) δ: 1.60–1.90(4H,m), 2.16–2.32(1H,m), 2.50–2.63(1H,m), 2.70–2.85(3H,m), 3.00–3.25(2H,m), 3.36 (1H, dd, J=9.5, 12.9 Hz), 3.82(3H,s), 4.10(1H, dd, J=3.4, 12.9 Hz), 5.20(1H, d, J=11.7 Hz), 5.33(1H, d, J=11.7 Hz), 6.70–7.35(12H,m)

Elemental analysis: for $C_{27}H_{30}N_2O_2$

Calculated (%): C, 78.23; H, 7.29; N, 6.76.

Found (%): C, 78.55; H, 7.16; N, 6.61.

Example 18

A hydrogen chloride ether saturated solution was added to a solution of 1.6 g (3.9 mmols) of (S)-(−)-5,11-dihydro-5-[1-(3-methoxyphenethyl)-2-pyrrolidinylmethyl]dibenzo[b,e][1,4]oxazepine in 20 ml of diethyl ether, and the mixture was stirred for 5 minutes. Then, the solvent was distilled off under reduced pressure. The resulting residue was recrystallized from acetone to give 0.93 g of (S)-(−)-5,11-dihydro-5-[1-(3-methoxyphenethyl)-2-pyrrolidinyl-methyl]dibenzo[b,e][1,4]oxazepine hydrochloride as a colorless prism crystal in a yield of 53%.

m.p.: 164–166° C.

$[\alpha]_D^{25}$ −2.1° (c=1.0, EtOH)

IR (nujol) ν max cm$^{-1}$: 2400, 1600, 1490, 1296, 1258

FAB/Mass: 415 [M+H]$^+$

NMR (CDCl$_3$) δ: 1.70–2.32(4H,m), 2.70–3.20(3H,m), 3.28–3.70(3H,m), 3.81(3H,s), 3.85–4.02(1H,m), 4.20–4.32 (1H,m), 4.58–4.75(1H,m), 5.16(1H, d, J=12.3 Hz), 5.31(1H, d, J=12.3 Hz), 6.70–7.40(12H,m), 12.8 (1H,b)

Elemental analysis: for $C_{27}H_{30}N_2O_2 \cdot HCl$

Calculated (%): C, 71.90; H, 6.93; N, 6.21.

Found (%): C, 71.90; H, 7.01; N, 6.03.

Preparation Examples are described below.

Example 19

(S)-(−)-5,11-dihydro-5-[1-phenethyl-2-pyrrolidinylmethyl]dibenzo[b,e][1,4]oxazepine hydrochloride as a yellow powder was synthesized using (R)-(−)-3-chloro-1-phenethylpiperidine as a same manner of Examples 5 and 6.

$[\alpha]_D^{25}$ +7.83° (c=0.99, EtOH)

IRνnujol max cm$^{-1}$: 2400 (NH$^+$), 1600, 1490, 1465

FAB/MS: m/z 385 [M+H]$^+$ $^1$H-NMR(CDCl$_3$) δ:1.80–2.35 (4H, m, pyrrolidinyl-C3, 4-H), 2.70–4.02 (7H, m, pyrrolidinyl-C2, 5-H+>N—CH$_2$—CH$_2$—Ar), 4.20–4.38 (1H, m,>N—CHH—CH<), 4.60–4.77 (1H, m,>N—CHH—CH<), 5.15 (1H, d, J=12.3Hz, —O—CHH—Ar), 5.30 (1H, d, J=12.3 Hz, —O—CHH—Ar), 6.75–7.40 (13H, m, Ar—H), 12.8 (1H, br, HCl)

Elemental analysis: for $C_{27}H_{28}N_2O_3 \cdot HCl$

Calculated (%): C, 74.18; H. 6.94; N, 6.65.

Found (%): C, 74.27; H, 6.99; N, 6.54.

Example 20

0.826 g (21.8 mmol) of sodium borohydride was added to 2-bromo-4'-methoxy-acetophenone (10 g, 43.7 mmol) in methanol (200 ml) and the mixture was stirred for 1 hour at room temperature. The mixture was concentrated in vacuo and saturated aqueous sodium chloride was added to the residue and the product was extracted with ethyl acetate. The organic layer was washed with saturated aqueous sodium chloride, dried over anhydrous magnesium sulfate, and concentrated in vacuo to give 2-bromo-1-(4'-methoxyphenyl) ethanol (11.05g).

To a mixture of 2-bromo-1-(4'-methoxyphenyl) ethanol (10.5 g, 45.5 mmol) and 5,6-dihydropyran (10.4 ml, 113 mmol) in dichloromethane (200 ml) was added catalytic amount of pTsOH-H$_2$O and the mixture was stirred for 30min at room temperature. The reaction mixture was poured into saturated aqueous sodium hydrogen carbonate and the product was extracted with ethyl acetate. The organic layer was washed with saturated aqueous sodium chloride, dried over anhydrous sodium sulfate, and concentrated in vacuo. The residue was purified by silicagel column chromatography (n-hexane:ethyl acetate=30: 1) to give 11.09 g (77.4%) of [2-bromoethyl-1-(4'-methoxyphenyl)] tetrahydropyranylether as yellow oil.

Mixture of (R)-(+)-2-pyrrolidinemethanol (3.50 g, 34.6 mmol) and [2-bromoethyl-1-(4'-methoxyphenyl)) tetrahydropyranylether (11.0 g, 3 5.2 mmol), sodium carbonate (4.40 g, 35.2 mmol), NaI (0.16 g, 1.04 mmol) in acetonitrile (100 ml) was heated at 50° C. for 40 hours. The mixture was concentrated in vacuo and the residue was purified by silicagel column chromatography (n-hexane:ethyl acetate= 1:5) to give 5.76 g (7 7.4%) of (2R)-(+)-2-hydroxymethyl-1-[4'-methoxyphenyl (2-15 tetrahydropyranyloxy)ethyl] pyrrolidine as yellow oil.

To a solution of 5.70 g (17.0 mmol) of (2R)-(+)-2-hydroxymethyl-1-[4'-methoxyphenyl (2-tetrahydropyranyloxy)ethyl]pyrrolidine and 4.74 ml of triethylamine (40.0mmol) in dichloromethane (100 ml) was added 2.37 ml (30.6 mmol) of methanesulfonylchloride and the mixture was stirred at room temperature for 16 hours. The mixture was diluted with dichloromethane and the solution was washed with water and saturated aqueous sodium chloride, dried over anhydrous sodium sulfate, and concentrated in vacuo. The residue was purified by silicagel column chromatography ((ethyl acetate)) to give 5.0 g (80%) of (3S)-(−)-3-chloro-[4-methoxyphenyl(2-tetrahydropyranyl)ethyl]piperidine as yellow oil.

(3S)-(−)-3-chloro-[4-methoxyphenyl(2-tetrahydropyranyl) ethyl]piperidine was coupled with 5,11-dihydrodibenzo[b,e][1,4]oxazepine as described in Example 1 to give 1.89 g (30%) and 1.50 g (24%) of the two diastereomers of (2R)-(−)-5,11-dihydro-5-[1-[4-methoxyphenyl (2-tetrahydropyranyloxy) ethyl]pyrrolidin-2-yl]methyl]dibenzo[b,e][1,4]oxazepine as yellow oil.

1.85 g (3.59 mmol) of the first eluting diastereomer in methanol (50 ml) was treated with 0.68 g (3.59 mmol) of pTsOH-H$_2$O and the mixture was stirred at room temperature for 16 hours. The solution was poured into saturated sodium hydrogen carbonate and the product was extracted with ethyl acetate. The organic layer was washed with saturated aqueous sodium chloride, dried over anhydrous magnesium sulfate, and concentrated in vacuo. 1.33 g (68%) of (2R)-(−)-5,11-dihydro-5-[1-[4-methoxyphenyl (2-hydroxy) ethyl] pyrrolidin-2-yl]methyl]dibenzo[b,e][1,4] oxazepine hydrochloride was obtained as colorless prisms by treateing the residue with ether saturated with hydrogen chloride.

$[\alpha]_D^{25}$ −22.5° (c=0.99, EtOH)

IR νnujol max cm$^{-1}$: 3224 (OH), 2472 (NH$^+$), 1610, 1514, 1488

FAB/MS: m/z 431[M+H]$^+$ $^1$H-NMR(CDCl$_3$) δ:1.73–2.19 (4H, m, pyrrolidinyl-C3, 4-H), 3.10–3.84 (8H, m, pyrrolidinyl-C2, 5-H+>N—CH$_2$—

CH(-0)—Ar+—OCH$_3$), 3.92–4.12 (1H, m,>N—CHH—CH<), 4.42–4.55 (1H, m,>N—CHH—CH<), 5.05–5.42 (3H, m, —OH+—O—CH$_2$—Ar), 6.13–6.24 (1H, m, >C—O—), 6.69–7.52 (12H, m, Ar—H), 10.9 (1H, br, HCl)

Elemental analysis: for C$_{27}$H$_{28}$N$_2$O$_3$.HCl
Calculated (%): C, 69.40; H, 6.69; N, 6.00.
Found (%): C, 69.29; H, 6.70; N, 5.93.

Example 21

0.593 ml of DMSO (8.36 mmol) in 3 ml of dichloromethane was added to 0.365 ml (4.18 mmol) of oxalyl chloride in dichloromethane (15 ml) and the mixture was stirred at −78° C. for 15 min. 1.2 g (2.79 mmol) of (R)-(−)-5,11-dihydro-5-[1-[4-methoxyphenyl (2-hydroxy) ethyl]pyrrolidin-2-yl]methyl]dibenzo[b,e][1,4]oxazepine in dichloromethane (5 ml) was added at −78° C. and after 2 hours 2.33 ml (1.67 mmol) of triethylamine in 5 ml of dichloromethane was added. The mixture was warmed to room temperature and the mixture was poured in to saturated sodium hydrogen carbonate. The products were extracted with dichloromethane and the organic layer as washed with water, saturated aqueous sodium chloride, dried over anhydrous magnesium sulfate, and concentrated in vacuo. The residue was purified by silicagel column chromatography (n-hexane:ethyl acetate=5:1 ) to give pale yellow oil. By treating the oil with ether saturated with hydrogen chloride gave 452 mg (35%) of (R)-(−)-5,11-dihydro-5-[1-[4-methoxyphenyl (2-oxo) ethyl]pyrrolidin-2-yl]methyl]dibenzo7[b,e][1, 4]oxazepine hydrochloride as yellow powder.

[α]$_D^{25}$ −8.1° (c=1.00, EtOH)
IR ν nujol max cm$^{-1}$: 2596 (NH$^+$), 1684 (C=O), 1602, 1514, 1492
FAB/MS: m/z 429[M+H]$^+$
$^1$H-NMR(CDCl$_3$) δ:1.90–2.53 (4H, m, pyrrolidinyl-C3, 4-H), 3.33–5.18 (11H, m, pyrrolidinyl-C2, 5-H+>N—CH$_2$—C(=0)—Ar+—OCH$_3$+—O—CHH—Ar), 5.32 (1H, d, J=12.9 Hz, —O—CHH—Ar), 6.62–7.43 (10H, m, Ar—H), 7.73–7.87 (2H, m, Ar—H), 12.9 (1H, br, HCl)

Elemental analysis: for C$_{27}$H$_{28}$N$_2$O$_3$.HCl
Calculated (%): C, 69.74; H, 6.29; N, 6.02.
Found (%): C, 68.59; H, 6.29; N, 5.68.

Example 22

3.27 g(27.5 mmol) of thionyl chloride was added dropwise to a suspension of cis-4-hydroxy-D-proline (3.00 g, 2.9 mmol) in ethanol (15 ml) and the mixture was refluxed for 2 hours. The mixture was concentrated, acetone was added to the residue and the solution was cooled on ice. The resultant precipitate was filtered and 4.23 g of (2R, 4R)-(+)-2-(ethoxycarbonyl)-4-hydroxypyrrolidine hydrochloride was obtained as colorless needles (94.5%).

To a suspension of 6.60 g (33.7 mmol) of (2R, 4R)-(+)-2-(ethoxycarbonyl)-4-hydroxypyrrolidine hydrochloride in acetonitrile (60 ml) were added 8.22 g (77.6 mmol) of sodium carbonate, 4-methoxyphenethyl bromide (8.71 g, 40.5 mmol), and sodium iodide (150mg, 1.0 mmol) and the mixture was stirred at 40–45° C. for 65 h. The mixture was concentrated in vacuo and water was added to the residue, and the products were extracted with ethyl acetate. The extract was washed with saturated aqueous sodium chloride and the products were extracted with 10% aqueous hydrochloride. The extract was washed with ethyl acetate, basified with potassium carbonate and extracted with ethyl acetate. The organic layer was washed with saturated aqueous sodium chloride, dried over anhydrous sodium sulfate, and concentrated in vacuo to obtain oily (2R, 4R)-(+)-2-(ethoxycarbonyl)-4-hydroxy-1-(4-methoxy phenethyl) pyrrolidine (5.85 g, 59.1%).

9.32 ml (123 mmol) of MOMCl was added to a solution of 25 ml (144 mmol) of N,N-diisopropylethylamine and 6.00 g (20.5 mmol) of (2R, 4R)-(+)-2-(ethoxycarbonyl)-4-hydroxy-1-(4-methoxyphenethyl) pyrrolidine in dichloromethane (100 ml) and the mixture was stirred for 14 hours at room temperature. The mixture was washed with saturated aqueous sodium carbonate and saturated aqueous sodium chloride, dried over anhydrous sodium sulfate, and concentrated in vacuo. The residue was purified by silicagel column chromatography (ethyl acetate : n-hexane=1:1 ) to give 6.20 g of (2R, 4R)-(+)-2-(ethoxycarbonyl)-4-(methoxymethoxy)-1-(4-methoxyphenethyl) pyrrolidine in 89.8% yield.

To an ice-cooled suspension of 690 mg of LiAlH$_4$ (18.1mmol) in 15 ml of dry ether was added 6.10 g (18.1 mmol) of (2R, 4R)-(+)-2-(ethoxycarbonyl)-4-(methoxymethoxy)-1-(4-methoxyphenethyl) pyrrolidine in 15 ml of dry ether and the mixture was stirred on ice for 30 min and at room temperature for 30 min. To the ice-cooled mixture 0.7 ml of water and 1N NaOH were added and the mixture was stirred for 30min on ice, and for 30 min at room temperature. Magnesium sulfate was added and after stirring for 30min, insoluble materials were filtered off on celite. The filtrate was concentrated in vacuo to give 5.30 g of (2R, 4R)-(+)-2-(hydroxymethyl)-4-(methoxymethoxy)-1-(4-methoxyphenethyl) pyrrolidine (99.3%) as pale yellow oil.

To a solution of 4.50 g (20.2 mmol) of (2R, 4R)-(+)-2-(hydroxymethyl)-4-(methoxymethoxy)-1-(4-methoxyphenethyl) pyrrolidine and 2.40 ml of triethylamine (23.8 mmol) in dichloromethane (35 ml) was added 2.62 ml (22.9 mmol) of methanesulfonylchloride and the mixture was stirred at room temperature for 4.5 hours. The mixture was diluted with dichloromethane and the solution was washed with saturated aqueous sodium carbonate and saturated aqueous sodium chloride, dried over anhydrous sodium sulfate, and concentrated in vacuo. The residue was purified by silicagel column chromatography (ethyl acetate : n-hexane=1:2 ) to give 4.82 g (87.2%) of (3S, 5R)-(+)-3-chloro-5-(methoxymethoxy)-1-(4-methoxyphenethyl) piperidine as colorless oil.

(3S, 5R)-(+)-3-chloro-5-(methoxymethoxy)-1-(4-methoxyphenethyl)piperidine was coupled with 5,11-dihydrodibenzo[b,e][1,4]oxazepine as described in Example 1 to give (+)-5,11-dihydro-5-[[(2R, 4R)-4-(methoxymethoxy)-1-(4-methoxyphenethyl)pyrrolidin-2-yl]methyl]dibenzo[b,e][1,4]oxazepine in 4.30 g (72.6%) yield as pale yellow oil.

4.20 g (8.85 mmol) of (+)-5,11-dihydro-5-[[(2R, 4R)-4-(methoxymethoxy)-1-(4-methoxyphenethyl)pyrrolidin-2-yl]methyl]dibenzo[b,e][1,4]oxazepine in 40 ml of methanol was treated with 20 ml of 10% HCl for 1 hour under reflux. Methanol was removed in vacuo and 1N NaOH was added to the residue. The products were extracted with ethyl acetate and the organic layer was washed with saturated aqueous sodium chloride, dried over anhydrous sodium sulfate, and concentrated in vacuo. The residue was purified by silicagel column chromatography (ethyl acetate ) to give 3.02 g (79.3%) of (+)-5,11-dihydro-5-[[(2R, 4R)-4-hydroxy-1-(4-methoxyphenethyl) pyrrolidin-2-yl]methyl]dibenzo[b, e][1,4]oxazepine as pale yellow amorphous.

Mixture of 660 mg (1.53 mmol) of (+)-5,11-dihydro-5-[[(2R, 4R) -4-hydroxy-1-(4-methoxyphenethyl) pyrrolidin-2-yl]methyl]dibenzo[b,e][1,4]oxazepine, 1.04 g (3.98 mmol), 486 mg (3.98 mmol) of benzoic acid, and 693 mg (3.98 mmol) of DEAD in tetrahydofuran (15 ml) was stirred for 20 hours at room temperature. The mixture was diluted with ether and the solution was washed with saturated aqueous sodium hydrogen carbonate, water, and saturated aqueous sodium chloride, dried over anhydrous sodium sulfate, and concentrated in vacuo. The residue was purified by silicagel column chromatography (ethyl acetate: n-hexane=1:1 ) to give 680 mg (83.3%) of (+)-5-[[(2R, 4S)-4-benzoyloxy-1-(4-methoxyphenethyl)pyrrolidin-2-yl] methyl]-5,11-dihydrodibenzo[b,e][1,4]oxazepine as pale yellow amorphous.

To 870 mg (1.63 mmol) of (+)-5-[[(2R, 4S)-4-benzoyloxy-1-(4-methoxy phenethyl)pyrrolidin-2-yl] methyl]-5,11-dihydrodibenzo[b,e][1, 4]oxazepine in 15 ml of ether was added 460 mg (11.4 mmol) of NaOH in methanol (60 ml) and the mixture was stirred at room temperature for 1 hour. The mixture was concentrated in vacuo, then water was added to the residue and the products were extracted with ether. The organic layer was washed with saturated aqueous sodium chloride, dried over anhydrous sodium sulfate, and concentrated in vacuo. The residue was purified by silicagel column chromatography (ethyl acetate) to give 680 mg (97.1%) of (+)-5-[[(2R, 4S)-4-hydroxy-1-(4-methoxyphenethyl) pyrrolidin-2-yl]methyl]-5,11-dihydrodibenzo[b,e][1,4]oxazepine as yellow amorphous.

$[\alpha]_D^{25}$ +33.6° (c=1.00, EtOH)

IR v film max cm$^{-1}$: 3430 (OH)

$^1$H-NMR δ:1.40–1.56 (1H, br, OH), 1.74–2.00 (2H, m, pyrrolidinyl-3-H), 2.33 (1H, dd, J=10.0, 5.2 Hz, pyrrolidinyl-5-H), 2.57–2.84 (3 H, m, NCHHCH$_2$Ar), 2.99–3.17 (2H, m, NCHHCH$_2$Ar, pyrrolidinyl-2-H), 3.34 (1H, dd, J=13.0, 9.2 Hz, NCHHCH), 3.45 (1H, dd, J=10.0, 5.6 Hz, pyrrolidinyl-5-H), 3.81 (3H, s, OCH$_3$), 4.11 (1H, dd, J=13.0, 3.0 Hz, NCHHC H), 4.30–4.44 (1H, m, pyrrolidinyl-4-H), 5.21 (1H, d, J=11.8 Hz, OCH H), 5.32 (1H d, J=11.8 Hz, OCHH), 6.73–6.86 (3H, m, Ar—H), 6.85 (2H, d, J=8.5 Hz, Ar—H), 6.92–7.12 (3H, m, Ar—H), 7.12 (2H, d, J=8.5 Hz, Ar—H), 7.22–7.35 (2H, m, Ar—H)

Elemental analysis: for C$_{27}$H$_{30}$N$_2$O$_3$.HCl

Calculated (%): C, 75.32; H, 7.02; N, 6.51.

Found (%): C, 76.99; H, 7.10; N, 6.27.

630 mg (1.46 mmol) of (+)-5-[[(2R, 4S)-4-hydroxy-1-(4-methoxyphenethyl)pyrrolidin-2-yl]methyl]-5,11-dihydrodibenzo[b,e][1,4]oxazepine in 5 ml of dichloromethane was treated with 0.5 ml of ether saturated with hydrogen chloride and the mixture was concentrated in vacuo. the residue was recrystalized from acetone-ether to give 690 mg (100%) of (+)-5-[[(2R, 4S)-4-hydroxy-1-(4-methoxyphenethyl) pyrrolidin-2-yl]methyl]-5,11-dihydrodibenzo-[b,e][1,4]oxazepine hydrochloride as colorless prisms.

$[\alpha]_D^{25}$ -2.5° (c=1.00, EtOH)

IR v nujol max cm$^{-1}$: 3255 (OH), 2800–2300 (NH$^+$)

FAB/MS (positive ion mode) m/z: 431 (M+H)$^+$.

$^1$H-NMR δ:2.00–2.20 (1H, m, pyrrolidinyl-3-H), 2.26 (1H, dd, J=13.1, 6.0 Hz, pyrrolidinyl-3-H), 2.93–3.33 (4H, m, NCHHCH$_2$Ar, pyrrolidinyl-5-H), 3.48–3.66 (2H, m, OH, pyrrolidinyl-2-H), 3.78 (3H, s, OCH$_3$), 3.84–4.02 (2H, m, NCHHCH$_2$Ar, pyrrolidinyl-5-H), 4.28 (1H, dd, J=14.1, 7.3 Hz, NCHHCH), 4.50–4.62 (1H, m, pyrrolidinyl-4-H), 4.58 (1H, dd, J=14.1, 6.1 Hz, NCHHCH), 5.15 (1H, d, J=12.4 Hz, OCHH), 5.36 (1H, d, J=12.4 Hz, OCHH), 6.78–6.95 (5H, m, Ar—H), 6.95–7.17 (5H, m, Ar—H), 7.20–7.38 (2H, m, Ar—H), 11.95–12.20 (1H, br, NH$^+$).

Elemental analysis: for C$_{27}$H$_{30}$N$_2$O$_3$.HCl

Calculated (%): C, 69.44; H, 6.69; N, 6.00.

Found (%): C, 69.94; H, 6.97; N, 5.92.

Examples of preparations will be described as follows:

Preparation Example 1

The following ingredients were mixed in a usual manner, and the mixture was formed into a tablet containing 50 mg of a main ingredient.

| | |
|---|---|
| Compound in Example 2 | 50 mg |
| lactose | 200 mg |
| crystalline cellulose | 40 mg |
| magnesium stearate | 5 mg |

Preparation Example 2

A mixture comprising the following ingredients was granulated in a usual manner to give granules.

| | |
|---|---|
| Compound in Example 2 | 50 mg |
| lactose | 90 mg |
| corn starch | 60 mg |
| talc | 30 mg |
| magnesium stearate | 10 mg |

The pharmacological test and the acute toxicity test of the compounds of the present invention are described below.

Test Example 1

In-vitro calcium channel antagonism (blood vessel):

The aorta of each of Crj:CD male rats (body weight of from 350 to 400 g) was extracted to form a spiral preparation. This blood vessel preparation was suspended in a Krebs-Henseleit solution of 37° C. which was oxygenated with a mixed gas (containing 95% oxygen and 5% carbon dioxide). The change in the tension of the blood vessel was isometrically recorded on a pen-writing recorder through a transducer. The high K$^+$-induced contraction was caused by changing the nutrient solution from a normal Krebs-Henseleit solution to a high K$^+$-Krebs solution (containing 78.9 mM NaCl, 43.8 mM KCl, 2.0 mM CaCl2$_1$ 1.2 mM MgSO$_4$, 1.2 mM K$_2$H$_2$ PO$_4$, 25 mM NaHCO$_3$ and 10 mM glucose). The test compound was incubated for 60 minutes. Compound A described in European Patent No. 0404359A1 was used as a comparative substance. The calcium channel antagonism was evaluated in terms of the concentration (IC$_{50}$) of the test compound showing the 50% inhibition of the contraction.

[A]

·HCl

Test Example 2

In-vitro calcium channel antagonism (ileum):

The ileum of each of Hartley-strain male guinea pigs (body weight: from 400 to 450 g) was extracted from a portion which was 5 cm apart from the ileocecum. This ileum preparation was suspended in a Krebs-Henseleit solution of 31° C. which was oxygenated with a mixed gas (containing 95% oxygen and 5% carbon dioxide). The change in the tension of the ileum was isometrically recorded on a pen-writing recorder. The high $K^+$-induced contraction was caused by adding 2 mM $CaCl2$ in a calcium-free and high $K^+$-Krebs solution (containing 43.9 mM NaCl, 78.8 mM KCl, 1.2 mM $MgSO_4$, 1.2 mM $K_2H_2PO_4$, 25 mM $NaHCO_3$ and 10 mM glucose). The test compound was incubated for 60 minutes. The calcium channel antagonism was evaluated in terms of the concentration ($IC_{50}$) of the test compound showing the 50% inhibition of the contraction. As is clear from Table 1, it is identified that the compound of the present invention is a calcium channel blocker having a high selectivity for the intestinal tract.

TABLE 1

| Test compound | Ca2+ channel antagonistic activity ($IC_{50}$, nM) | |
| --- | --- | --- |
|  | rat aorta | guinea pig ileum |
| Example 2 | 250 | 85 |
| Compound A | 360 | 180 |

Test Example 3

In-vivo test [effect of inhibiting acceleration of stool excretion in a wrap restraint stress (WRS) model]:

The test was conducted by the method of William et al. [Gastroenterology, 94, 611 (1988)]. That is, each of Crj:CD male rats (from 6 to 7 weeks old) was slightly etherized, and the fore shoulder, the foreleg and the chest thereof were wrapped with a paper tape to apply stress thereto. The rat was allowed to stand under stress for 1 hour, and the amount of stool excreted during that time was measured. The test compound was orally administered to the rat 30 minutes before applying the stress thereto. The normal group was etherized, and then allowed to stand for 1 hour without applying stress thereto. Thereafter, the amount of stool excreted was measured. In this test, nicardipine and Compound A were used as comparative substances. The 50% inhibition dose ($ID_{50}$) relative to the increase in the body weight of stool owing to WRS was calculated by the Litchfield-Wilcoxon method, and the results are shown in Table 2-1. In addition, and inhibition of test compounds (lomg/kg, p.o.) expressed as a percentage of control were determined and the results were shown in Table 2—2.

Test Example 4

Decrease in the blood pressure in rats:

This test was conducted by the tail cuff method. That is, each of Crj:CD male rats (from 8 to 9 weeks old) had been warmed to fully expand the tail artery. The tail artery pressure was then measured immediately before, and 1 hour after, the oral administration of the test compound using a non-invasive blood pressure measuring device. In this test, nicardipine and Compound A were used as comparative substances. With respect to the decrease in the blood pressure, a dose at which to cause the decrease in the blood pressure by 20 mmHg from the blood pressure immediately before the administration was calculated as $ED_{20}$ from the regression line of the decrease (mmHg) in the blood pressure relative to the logarithm of the dose of the test compound. The results are shown in Table 2-1. As is clear from Tables 2-1 and 2—2, the compound of the present invention has a higher selectivity for the intestinal tract than Compound A, and it can be an excellent agent of improving an abnormal moving function of the digestive tract.

TABLE 2-1

| Test compound | Inhibitory effect on WRS-induced defecation ($ID_{50}$, mg/kg, p.o.) | Hypotensive effect ($ED_{20}$, mg/kg, p.o.) |
| --- | --- | --- |
| Example 2 | 3.1 | >1000 |
| Example 4 | 1.8 | >1000 |
| Compound A | 34.8 | >100 |
| nicardipine | 6.8 | 4.0 |

TABLE 2-2

| Test compound | Inhibition rate (%) |
| --- | --- |
| Compound A | 20.0 |
| Compound 2 | 59.7 |
| Compound 4 | 65.6 |
| Compound 8 | 48.0 |
| Compound 12 | 60.0 |
| Compound 14 | 55.4 |
| Compound 21 | 45.8 |

Test Example 5

Anticholinergic activity by mydriasis of rats:

A suspension of 300 mg/kg of a test compound in 0.5% methyl cellulose was orally administered to each of Crj:CD male rats (from 7 to 8 weeks old). The diameter of the pupil after 1, 2 or 6 hours was measured using a stereoscopic microscope of 5x magnification. The results are shown in Table 3. As is clear from Table 3, it is identified that the compound of the present invention exhibits almost no anticholinergic activity as a side effect, compared to Compound A.

TABLE 3

| Test compound | rat pupillary diameter (mm) | | | |
| --- | --- | --- | --- | --- |
|  | before | 1 hour | 2 hours | 6 hours |
| Example 2 | 0.97 | 0.90 | 0.77 | 0.97 |
| Example 4 | 0.80 | 0.70 | 0.57 | 0.70 |
| Compound A | 0.85 | 2.18 | 2.27 | 2.62 |

Test Example 6

Decrease in the body temperature of rats:

A suspension of 100 mg/kg of a test compound in 0.5% methyl cellulose was orally administered to each of Crj:CD male rats (from 7 to 8 weeks old), and the body temperature (temperature of the rectum) after 1, 2 or 5 hours was measured using a thermistor thermometer, and the difference in the body temperature between the compound of the present invention and the comparative substance is shown in Table 4. As is clear from Table 4, it is identified that the compound of the present invention shows almost no decrease in the body temperature as a side effect compared to Compound A.

TABLE 4

| Test compound | change in body temperature | | |
|---|---|---|---|
| | 1 hour | 2 hour | 5 hour |
| Example 2 | 0 | −0.1 | −0.2 |
| Example 4 | −0.3 | −0.2 | +0.1 |
| Compound A | −0.5 | −0.6 | −0.5 |

Test Example 7

Acute toxicity test:

A suspension of a test compound in 0.5% methyl cellulose was intraperitoneally administered to each of ddy-strain male mice (4 weeks old) which had been fasted for 24 hours, and a mortality was observed for 7 days. A 50% lethal dose ($LD_{50}$) was calculated, and the results are shown in Table 5. As is clear from Table 5, it is identified that the compound of the present invention exhibits a low toxicity compared to Compound A.

TABLE 5

| Test compound | 50% lethal dose ($LD_{50}$, mg/kg, i.p.) |
|---|---|
| Example 2 | 175 |
| Example 4 | >200 |
| Example 12 | >280 |
| Compound A | 162.5 |

Test Example 8

Test for a toxicity in continuous administration for 1 week:

A suspension of 100 mg/kg of the compound in Example 2 or 12 in 0.5% methyl cellulose was orally administered to each of Crj:CD male rats (6 weeks old) continuously for 1 week at a rate of one administration per day to observe general conditions, to measure the body weight, to conduct biochemical inspection of the blood, to measure the weights of the internal organs and to conduct pathological inspection. As a result, no remarkable change was observed. Therefore, it was identified that the compound of the present invention exhibited a low toxicity.

As is apparent from the above-mentioned Test Examples, the compound of the present invention can give an excellent effect as an agent for treating intestinal diseases such as digestive tract abnormal moving function diseases, especially, an irritable bowel syndrome.

What is claimed is:

1. A method for treating or preventing an irritable bowel syndrome, which comprises administering an effective amount of a pharmaceutical composition, wherein said pharmaceutical composition comprises a 5,11-dihydrodibenzo[b,e][1,4]oxazepine compound represented by formula (I), a stereoisiomer thereof, a pharmacologically acceptable salt thereof, or a hydrate thereof as an active ingredient:

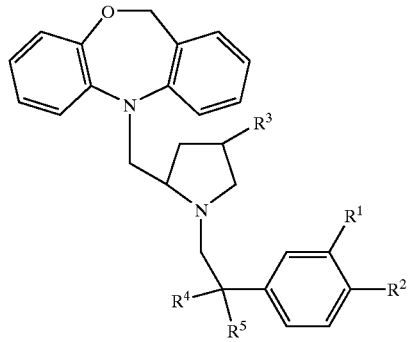

[I]

wherein $R^1$ and $R^2$ are the same or different and each represents a hydrogen atom, a halogen atom, a cyano group, a hydroxy group or a lower alkoxy group, or $R^1$ and $R^2$ together form —$O(CH_2)_nO$— in which n is 1, 2 or 3, $R^3$ represents a hydrogen atom or hydroxy group, $R^4$ and $R^5$ are the same or different and each represents a hydrogen atom or hydroxy group, or $R^4$ and $R^5$ together form =O group.

2. The method of claim 1, wherein the compound is in R form.

3. The method of claim 1, wherein $R^3$, $R^4$ and $R^5$ in the formula (I) each represents a hydrogen atom.

4. The method of claim 3, wherein the compound is in R form.

5. The method of claim 3 wherein $R^1$ represents a hydrogen atom, and $R^2$ represents a halogen atom or a lower alkoxy group.

6. The method of claim 5, wherein the compound is in R form.

7. A method for treating or preventing an irritable bowel syndrome, which comprises administering an effective amount of a pharmaceutical composition, wherein said pharmaceutical composition comprises (R)-(+)-5,11-dihydro-5-[1-(4-methoxyphenethyl)-2-pyrrolidinyl-methyl]dibenzo[b,e][1,4]oxazepine, a pharmacologically acceptable salt thereof, or a hydrate thereof.

8. A method for treating or preventing an irritable bowel syndrome, which comprises administering an effective amount of a pharmaceutical composition, wherein said pharmaceutical composition comprises (R)-(+)-5,11-dihydro-5-[1-(4-fluorophenethyl)-2-pyrrolidinyl-methyl]dibenzo[b,e][1,4]oxazepine, a pharmacologically acceptable salt thereof, or a hydrate thereof.

* * * * *